United States Patent

Heck et al.

[11] Patent Number: 6,142,981
[45] Date of Patent: Nov. 7, 2000

[54] HEMOSTASIS VALVE

[75] Inventors: Alicia F. Heck, St. Louis Park; Mark D. Krueger, Brooklyn Park, both of Minn.

[73] Assignee: Daig Corporation, Minnetonka, Minn.

[21] Appl. No.: 08/782,019

[22] Filed: Jan. 7, 1997

[51] Int. Cl.[7] ................................................... A61M 5/00
[52] U.S. Cl. ................................. 604/256; 604/167
[58] Field of Search .................................. 604/246, 256, 604/164, 167, 169; 137/846–850; 251/149.1

[56] References Cited

U.S. PATENT DOCUMENTS

| | | |
|---|---|---|
| 4,000,739 | 1/1977 | Stevens . |
| 4,341,239 | 7/1982 | Atkinson . |
| 4,436,519 | 3/1984 | O'Neill . |
| 4,610,665 | 9/1986 | Matsumoto et al. . |
| 4,649,904 | 3/1987 | Krauter et al. ............................. 128/6 |
| 4,653,477 | 3/1987 | Akui et al. . |
| 4,655,752 | 4/1987 | Honkanen et al. . |
| 4,673,393 | 6/1987 | Suzuki et al. . |
| 4,809,679 | 3/1989 | Shimonaka et al. . |
| 4,850,953 | 7/1989 | Haber et al. ............................. 600/32 |
| 4,909,798 | 3/1990 | Fleischhacker et al. . |
| 4,932,633 | 6/1990 | Johnson et al. . |
| 4,946,133 | 8/1990 | Johnson et al. . |
| 4,960,412 | 10/1990 | Fink . |
| 4,966,197 | 10/1990 | Jaron et al. ............................. 137/846 |
| 4,968,308 | 11/1990 | Herlitze et al. . |
| 5,059,186 | 10/1991 | Yamamoto et al. . |
| 5,092,857 | 3/1992 | Fleischhacker . |
| 5,104,376 | 4/1992 | Nakamura et al. ...................... 604/111 |
| 5,106,054 | 4/1992 | Mollenhauer et al. . |
| 5,114,408 | 5/1992 | Fleischhacker et al. . |
| 5,211,634 | 5/1993 | Vaillancourt . |
| 5,269,764 | 12/1993 | Vetter et al. . |
| 5,300,032 | 4/1994 | Hubbs et al. . |
| 5,304,156 | 4/1994 | Sylvanowicz et al. . |
| 5,456,284 | 10/1995 | Ryan et al. . |
| 5,542,923 | 8/1996 | Ensminger et al. . |

FOREIGN PATENT DOCUMENTS

| | | |
|---|---|---|
| 344907 | 6/1989 | European Pat. Off. . |
| 0 551 017 | 7/1993 | European Pat. Off. . |

Primary Examiner—Wynn Wood Coggins
Assistant Examiner—Deborah Blyveis
Attorney, Agent, or Firm—Scott R. Cox

[57] ABSTRACT

A one-piece hemostasis valve located within a longitudinally extended housing, with the valve comprising an extended sealing neck having a passageway therethrough, communicating with a sealing chamber having opposing sealing exit lips and preferably support shoulders on the outside of the valve adjacent to the sealing neck to provide support for the valve. The passageway of the extended sealing neck contains narrowed and broadened portions to prevent blood loss when receiving a guidewire and catheter inserted through the passageway of the sealing neck.

25 Claims, 5 Drawing Sheets

HEMOSTASIS VALVE

FIELD OF INVENTION

This invention relates to hemostasis valves. More particularly, this invention relates to an improved hemostasis valve containing a receiving area, a sealing chamber, sealing exit lips and a sealing neck between the receiving area and the sealing chamber, wherein the sealing neck contains broadened and narrowed portions which permit the introduction of different sized guidewires and catheters to pass through the valve with reduced resistance during passage.

BACKGROUND OF INVENTION

The introduction of catheters into blood vessels for a variety of purposes such as coronary angiography has been known for many years. Several techniques for introducing these catheters are available. One such technique is the cut-down method. Another is the Seldinger technique. This technique involves surgically opening a vein or artery with a needle, inserting a guidewire into the vein or artery through the lumen of the needle, withdrawing the needle, inserting over the guidewire a dilator located inside an associated sheath with a hemostasis valve, removing the dilator and inserting a catheter through the sheath and into the blood vessel.

Various types of hemostasis valves have been known in the prior art. However, in most cases, each hemostasis valve is designed for use with a specific size of catheter. Because adequate sealing around the catheter walls cannot be obtained for a variety of catheters having varying diameters using conventional hemostasis valves, it has not been possible to employ a single hemostasis valve with catheters of widely varying diameters.

These problems are particularly acute when the guidewire technique is used. Guidewires are of extremely small diameter, often as small as 0.025 inch (0.064 cm.). However, many catheters are relatively larger in diameter, for example, as large as about 0.120 inch (0.30 cm.) in diameter. Therefore, in the prior art it has been difficult to design a single hemostasis valve which will seal around both relatively large diameter catheters as well as relatively small diameter guidewires.

One method of solving this problem is shown in U.S. Pat. No. 5,092,857 which discloses a universal hemostasis cannula with hemostasis valve contained within a longitudinally extended valve housing, having a first opening and a central longitudinal passage communicating with an opposite second opening. This one-piece hemostasis valve comprises a receiving area, a sealing neck and a sealing chamber having opposite sealing exit lips with a support shoulder on the outside of said seal adjacent to the sealing neck to provide support for the seal. The support shoulder reduces the insertion and withdrawal force necessary for inserting dilators and guidewires of varying sizes through the cannula while still providing good "feel" for the medical practitioner when utilizing these products.

Another method of solving this particular problem is shown in U.S. Pat. No. 4,909,798 which discloses a universal hemostasis cannula with a hemostasis valve similar in design to that shown in U.S. Pat. No. 5,092,857 but without support shoulders. This valve has also solved some of the problems relating to sealing around extremely small diameter of guidewires with the relatively larger diameter of catheters, catheter introducers and dilators.

Another universal hemostasis valve is disclosed in U.S. Pat. No. 5,114,408. This device utilizes a one-piece seal located within a valve housing wherein the seal contains a sealing neck having a relatively small opening which communicates with a slit contained in a concave exit base of the seal. This valve has also been successful in solving some of the problems relating sealing around the extremely small diameter of guidewires used with the relatively larger diameter of catheters, catheter introducers and dilators.

Another method of solving this problem is disclosed in EP A2 0 344 907. This European patent application discloses a self-sealing catheter and guidewire introducer with a self-sealing gasket adapted to create a seal when a catheter or guidewire extends through the gasket. The sealing means disclosed by this application contains an outer half thickness and an inner half thickness which vary to permit the gasket to seal both smaller diameter guidewires and larger diameter catheters. A similar device is shown in U.S. Pat. No. 5,304,156.

Another hemostasis valve designed for use with a guidewire and catheter is disclosed in U.S. Pat. No. 4,946,133. This valve contains a cylindrical base having a central opening and a hollow convex dome-shaped member projecting from the base wherein the dome-shaped member has a slit formed in its external surface which extends inwardly to form a central self-sealing passage aligned with the central bore of the cylindrical base member. A similar device is shown in U.S. Pat. No. 5,106,054.

Another catheter introducer valve assembly is disclosed in U.S. Pat. No. 4,960,412 which discloses a first and second valve for preventing the flow of blood both when a catheter is inserted through the valve and when there is no catheter present. Similar devices are shown in U.S. Pat. Nos. 5,269,764, 5,211,634, 5,456,284 and 4,932,633.

Other devices designed to solve the problem of various sizes of catheters introduced as part of a surgical procedure have been disclosed, for example, in U.S. Pat. No. 4,000,739 which employs two gaskets to seal against the back pressure of blood in the cannula unit. The first, donut-shaped, gasket is provided with a hole slightly smaller than the diameter of the catheter to be inserted, while the second gasket is provided with a Y-shaped slit. However, when guidewires or catheters which are too small in diameter are inserted into this hemostasis valve, the sealing advantages of the first, donut-shaped gasket are no longer available because the larger diameter donut hole will not seal around the smaller diameter guidewire or catheter. Moreover, when catheters are employed having diameters which are extremely large in relation to the diameter of the hole in the donut-shaped gasket, the gasket may become separated from the hemostasis valve body or it may be unduly stretched so that it will not seal properly when a smaller sized catheter is inserted at a later time.

Hemostasis valves having similar problems to those discussed in U.S. Pat. No. 4,000,739 are disclosed in U.S. Pat. Nos. 4,673,393 and 4,610,665.

U.S. Pat. No. 4,436,519 discloses a seal containing a combination of a donut-shaped gasket and a cup-shaped gasket. As in other prior art seals where two gaskets are utilized to form the seal, the device described in the '519 patent suffers the same deficiencies because its donut-shaped gasket can only accept catheters having a limited range of diameter sizes. Moreover, this device is particularly susceptible to leakage when only a guidewire is in place.

U.S. Pat. No. 4,341,239 discloses a combination check-over-pressure relief valve similar in design to the '519 device containing a cylindrical main body portion which is supported by a radially outwardly extending flange and ribs as a stiffening means, wherein the ribs project from the surface of the main body portion.

U.S. Pat. No. 4,655,752 discloses a surgical cannula which does not employ donut-shaped gaskets. However, this cannula, like the other prior art cannulas, suffers from a lack of universality and from poor sealing. While two seals are employed, the second seal may only be used with catheters having a limited range of diameters and will provide little or no sealing for a guidewire.

German Patent No. 3,042,229 sets forth a hemostasis valve which may be used with catheters having a variety of diameters. However, it is extremely difficult to use this valve when relatively large diameter catheters are employed because the second seal is required to expand against the sidewalls of the cannula, thereby significantly increasing friction during insertion and the risk of hemodynamic dampening. Moreover, the sealing means of the device described in the '229 patent is formed from two separate pieces thereby increasing the difficulties of manufacture and the likelihood that one of the seals may become dislodged particularly during use with large sized catheters. A similar device is shown in U.S. Pat. No. 4,809,679.

Another problem shown by many prior art hemostasis cannulas is that the cardiologist must be able to "feel" the catheter as it is inserted through the gaskets or other sealing members of the hemostasis valve and ultimately into a blood vessel. If insertion of the catheter through the hemostasis valve is too difficult, the cannula unit may be rejected by cardiologists as being difficult to use during catheter insertion. Concomitantly, the use of hemostasis valves which exert undue pressure on the side walls of inserted catheters may lead to excessive hemodynamic dampening of the catheter. In other words, excessive pressure on the exterior side-walls of a catheter may cause a narrowing of the catheter's diameter, thereby altering measurement parameters within the catheter.

In addition, hemostasis valves have also experienced problems from collapse of a portion or portions of the valve during the withdrawal of the dilator and the insertion of the catheter. Further, repeated insertion and withdrawal of catheters and catheter related devices through conventional hemostasis valves has become more and more difficult. This increase in force which is necessary for insertion and withdrawal further reduces the usability of conventional hemostasis valves.

Accordingly, it is one aspect of this invention to prepare a hemostasis valve unit.

Another aspect of this invention is to prepare a hemostasis valve which permits the easy insertion and withdrawal of both guidewires and catheters.

Another aspect of the invention is to prepare a hemostasis valve which has sufficient strength not to collapse on repeated insertions and withdrawals of catheters.

Another aspect of this invention is to prepare a hemostasis valve which is universal in nature and may be used with a wide variety of both large and small diameter guidewires and catheters, without leakage.

It is another aspect of this invention to prepare a hemostasis valve which will not leak when a guidewire is inserted into a vein or artery through the valve.

Another aspect of this invention is to prepare a hemostasis valve which is universal in nature and which does not exert undue pressure on the side walls of an inserted catheter while still providing support for the valve in use.

It is a further aspect of this invention to prepare a hemostasis valve having a unitary sealing member forming at least two separate sealing sections.

It is yet another aspect of this invention to construct a hemostasis cannula unit which will permit the use of catheters having a wide variety of diameters, while at the same time allowing insertion of any of these catheters without undue pressure/friction thereby providing good surgical "feel" for all diameters of catheters.

These and other aspects are obtained by constructing the hemostasis cannula units of the present invention.

SUMMARY OF INVENTION

The present invention involves a hemostasis valve housing unit which in one embodiment includes a longitudinally extended housing having first and second opposing open ends; a cap enclosing the first end and having an opening to permit insertion of a dilator or catheter into the longitudinally extended housing; and a valve located within the central passage of the longitudinally extended housing. The valve is provided with a sealing neck and sealing exit lips arranged so that a catheter may be readily inserted through the sealing neck and out the sealing exit lips. The sealing neck is elongated with a passageway passing therethrough. The sealing neck passageway contains narrowed and broadened portions where the diameter of the narrowed portion of the opening is smaller than the diameter of the broadened portion of the opening. The sealing neck is preferably supported by support shoulders which support the valve during the insertion of catheters or guidewires through the valve and on their withdrawal. The second end of the valve housing is attached to a sheath which is inserted into the vasculature.

DETAILED DESCRIPTION OF INVENTION

Figure 1:
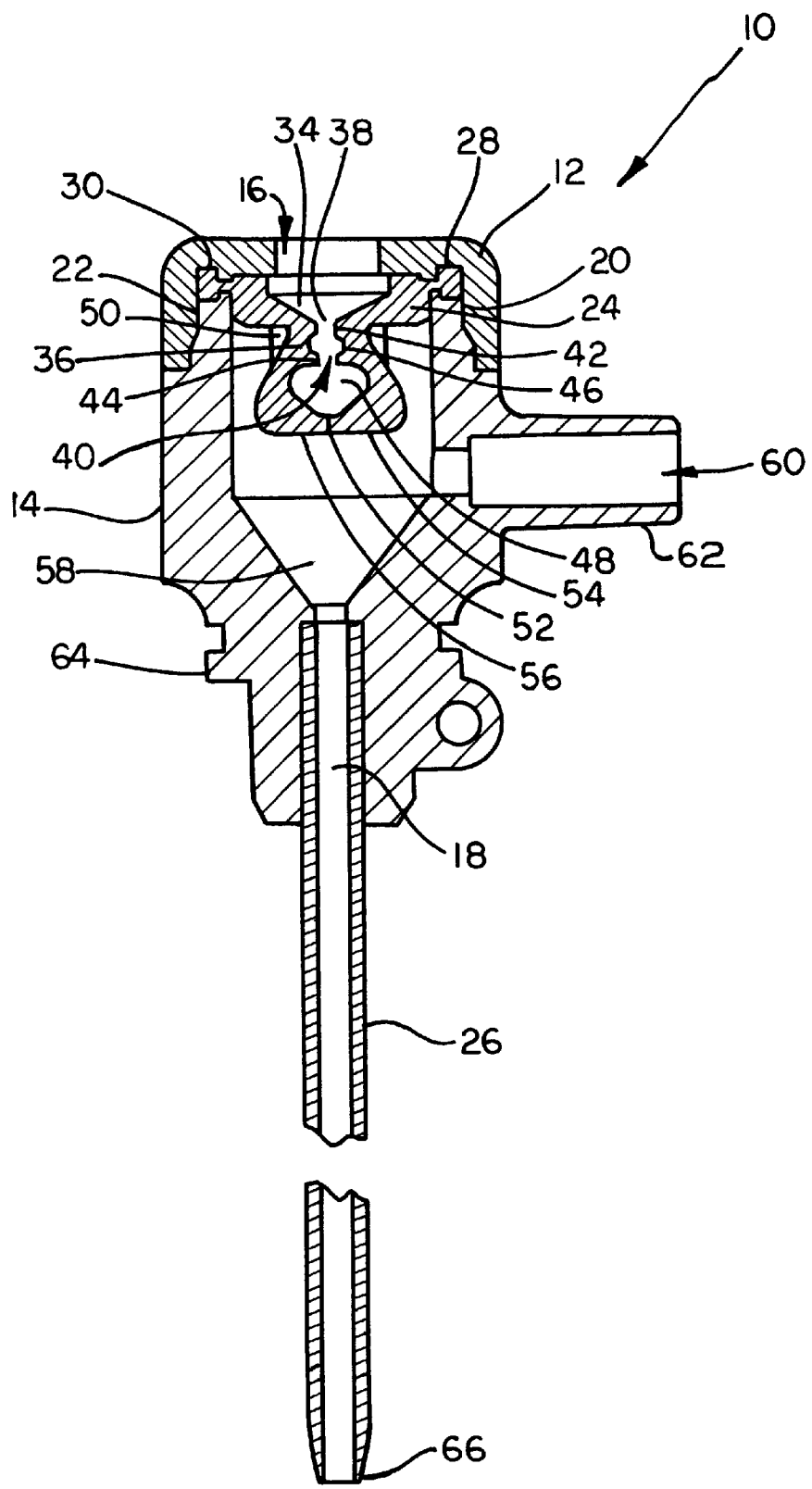
FIG. 1 is a cross-sectional view of a hemostasis cannula unit with hemostasis valve according to the present invention.

FIG. 1 shows a cross-sectional view of the hemostasis cannula unit of this invention. The cannula unit (10) is formed from four major parts. The cap (12) is attached to the top of the longitudinally extended valve housing (14). The valve housing (14) has first (16) and second (18) opposing open ends to permit insertion of a catheter into and out of the interior of the valve housing (14). The cap (12) and the valve housing (14) are formed from a relatively hard plastic, such as polycarbonate. The cap (12) may be secured to the valve housing by gluing, heat sealing, but preferably by mechanically attaching to the valve housing using for instance threads, clips or, as shown in the drawings, snap fitting (20) which is a circular ridge within the cap and groove (22). However, the preferred method of securing the valve housing (14) and the cap (12) uses ultrasonic bonding. The cap (12) and the valve housing (14) are first molded with respective interference fits and then ultrasonically bonded together. The hemostasis cannula unit (10) also includes the valve (24), which is formed from a pliant, resilient, rubber such as silicone rubber or latex rubber having a durometer range of about 20–60 (Shore A), which can be shaped to readily allow the passage of various sized guidewires and catheters. In a preferred embodiment a one piece valve is used, although a two piece, moldable valve may also be used. The hemostasis cannula unit (10) also contains a tube sheath (26) which is formed from a relatively rigid plastic, such as polytetrafluoroethylene (Teflon®), polyurethane, or polyethylene, or may be comprised of a composite plastic with an additional material, such as a braid for support. The sheath (26) is inserted within the valve housing (14) and cooperates to provide an exit from the interior of the valve housing (14).

As shown in FIG. 1, the valve (24), the cap (12) and the valve housing (14) are joined together by inserting the valve (24) into the cap (12) such that the uppermost edge (28) of the valve (24) is fully inserted within the cap (12) and rests against the rib (30), which is preferably circular in nature. The cap (12) with the valve (24) in position is then placed on top of the valve housing (14). The valve (24) is inserted inside the valve housing (14), and downward pressure is applied to the cap (12) along with ultrasonic energy to bond the cap to the housing. With the cap (12) and housing (14) engaged, downward pressure on the cap (12) is maintained causing compression of the uppermost edge (28) of the valve (24) by the rib (30) which serves to hold the valve (24) in place within the valve housing (14).

The cap (12) is provided with a first opening (16) at the top, which can receive a dilator (not shown) that is inserted within the hemostasis cannula unit for purposes of introduction into body vessels.

The valve (24) has a conical receiving area (34) which tapers into a sealing neck (36) having a neck opening (38). Taken together the conical receiving area (34) and neck opening (38) provide for easy insertion of a catheter into the valve (24) and through the neck opening (38), with good "feel" and a minimization of hemodynamic pressure dampening.

Figure 2:
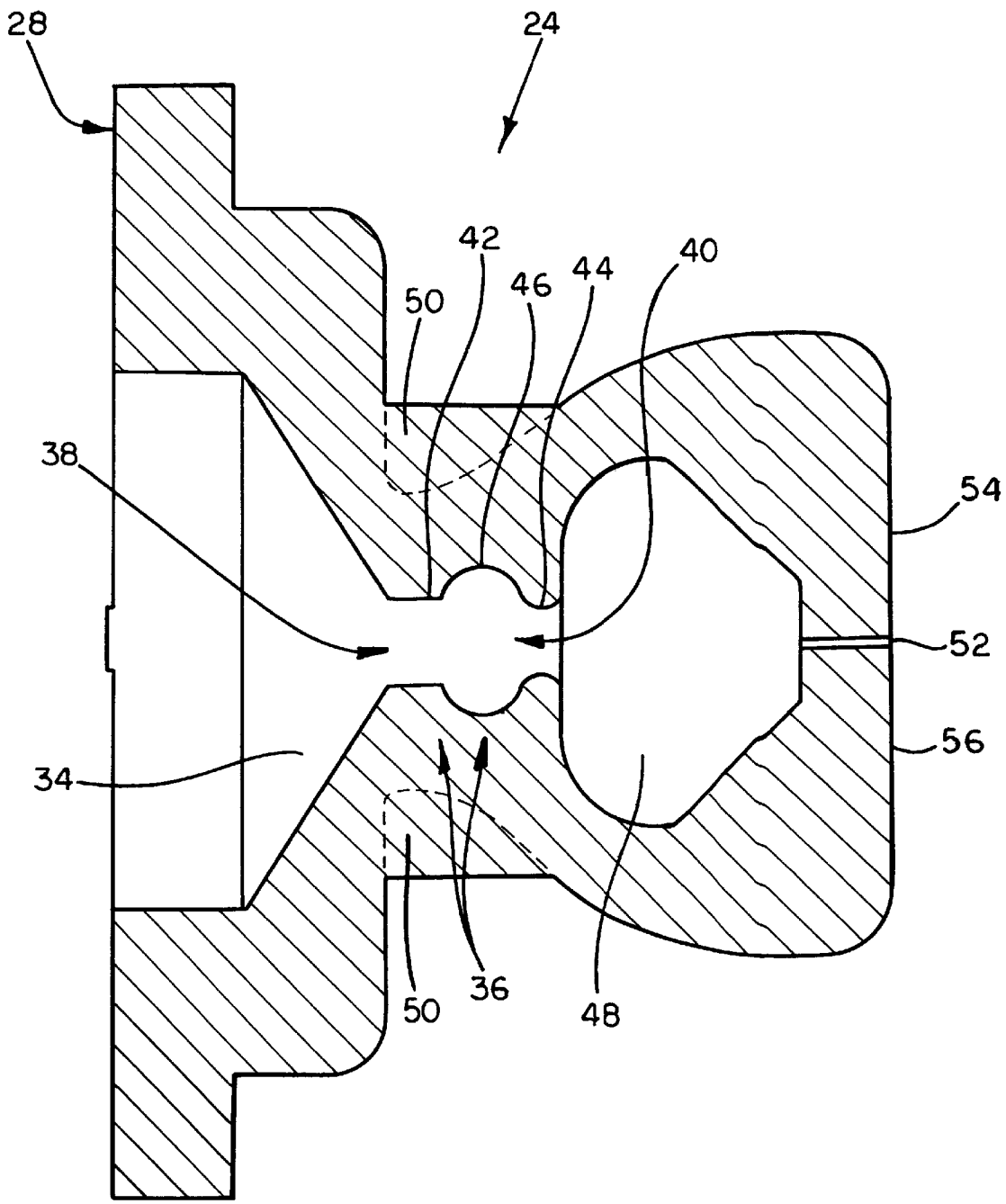
FIG. 2 is a cross-sectional view of the first embodiment of the hemostasis valve.

To enhance the good "feel" and minimize hemodynamic pressure dampening, the preferred sealing neck (36) as shown in FIG. 2 is longer than a conventional sealing neck such as disclosed in U.S. Pat. No. 5,092,857, with a passageway (40) therethrough containing narrowed and broadened portions. In one preferred embodiment, the sealing neck (36) contains a first narrowed portion (42) in communication with the conical receiving area (34), a second narrowed portion (44) in communication with a sealing chamber (48) and a broadened portion (46) between these two narrowed portions.

The diameter of the opening of the narrowed portion (42, 44) is slightly less than the diameter of a conventional guidewire which will pass through this seal. Preferably, narrowed portion 44 is slightly smaller than narrowed portion 42, although narrowed portion 42 may be larger than or the same diameter as narrowed portion 44. In conventional seals, the diameter of the sealing neck is the same throughout its length. See, for example, U.S. Pat. No. 5,092,857. By reducing the amount of the inner surface area of the sealing neck (36) which contacts a guidewire or catheter as it passes through the passageway (40) of the sealing neck (36), resistance to the movement of the guidewire or catheter through the sealing neck (36) is also reduced. Notwithstanding this reduced resistance, a good seal is still created against bleeding because of the presence of the narrowed portions of the sealing neck (36) which continue to press against the guidewire as it passes through the valve (24). The amount of the resistance to the movement of the guidewire or catheter through the valve (24) is directly related to the amount of material of the valve (24) in the sealing neck (36) which contacts the guidewire or catheter as it passes through the seal. By reducing the amount of this seal material to a minimum while at the same time retaining hemostasis around the guidewire or catheter while passing through the sealing neck (36), good "feel" is provided while at the same time minimizing hemodynamic pressure dampening.

Figure 3:
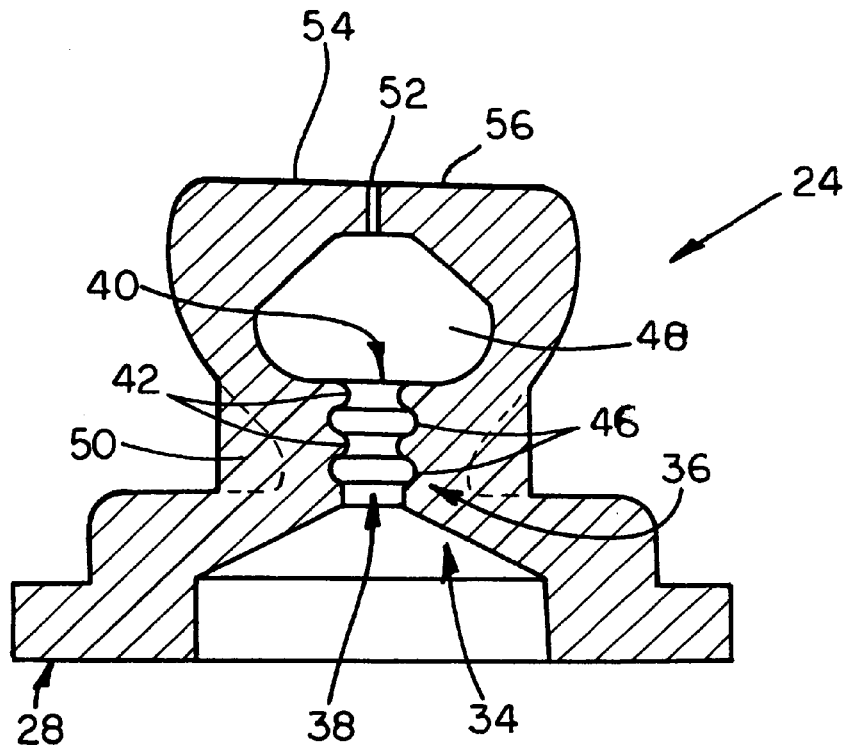
FIG. 3 is a cross-sectional view of a second embodiment of the hemostasis valve.

A second embodiment of the seal is shown in FIG. 3. In this embodiment instead of two narrowed portions and a single broadened portion, three narrowed portions (42) and two broadened portions (46) are present with a broadened portion (46) placed between a pair of adjacent narrowed portions (42). The diameter of the narrowed (42) and broadened portions (46) of this second embodiment may be the same or different from the diameter of the narrowed and broadened portions of the first embodiment, with an enhanced "feel" resulting. Further, the diameter of narrowed portions 42 or broadened portions 46 may all be the same, or portions 42,44 may vary in sizes, some being larger or smaller in diameter.

Figure 4:
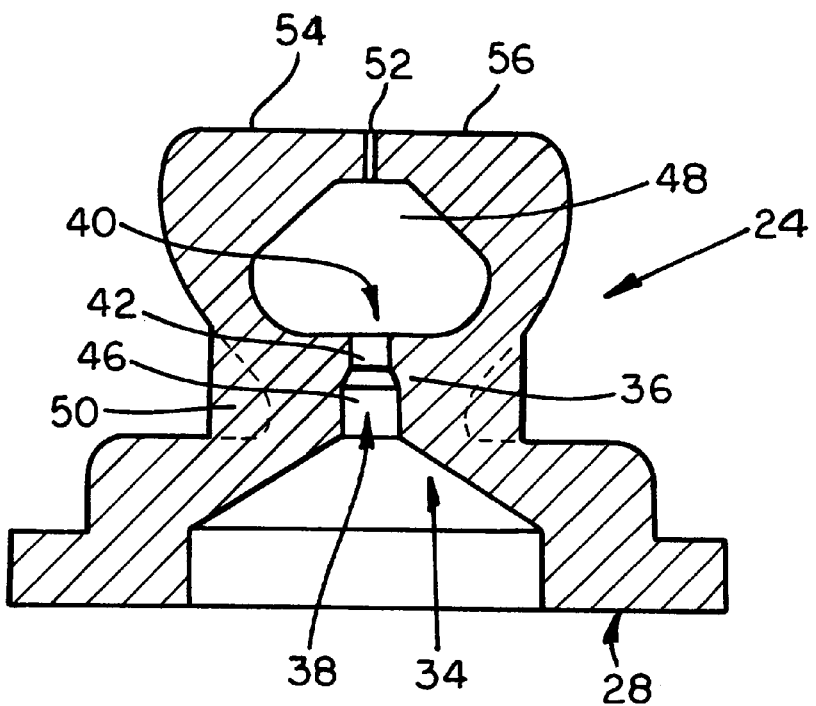
FIG. 4 is a cross-sectional view of a third embodiment of the hemostasis valve.

In a third embodiment as shown in FIG. 4, a single narrowed portion (42) and a single broadened portion (46) are present, wherein the single broadened portion (46) is preferably in communication with the conical receiving area (34). The diameter of the narrowed portion (42) is less than the diameter of a conventional guidewire that is to be used with the valve. The relative length of the narrowed portion (42) within the sealing neck (36) is about half the overall length of the passageway (40) of the sealing neck (42). Alternatively, the broadened portion (46) may be in communication with the sealing chamber (48) while the narrowed portion (42) is in communication with the conical receiving area (34).

Other embodiments of this invention can be visualized whereby the amount of material of the sealing neck (36) which comes in contact with the guidewire is reduced while still retaining a narrowed portion of the sealing neck firmly against an inserted guidewire as it passes through the sealing neck (36) to prevent blood loss.

Communicating with the conical receiving area (34) and the neck opening (38) is the sealing chamber (48) which may be of any convenient shape, although preferably, it is semi-spherical or flattened spherical in shape. The interior diameter of the sealing chamber (48) is preferably the same as the largest outside diameter of any catheter which will be employed with the hemostasis cannula unit (10) of this invention. In the preferred embodiment the diameter of the narrowed portion (44) of the sealing neck (36) closest to the sealing chamber (48) should be slightly smaller than that of any guidewire which will be employed so as to provide for sealing against the reverse flow of blood which may enter into the sealing chamber (48) while a guidewire is in place in the cannula unit (10).

In order to provide support for the valve when a catheter is inserted through the sealing neck (36), in a preferred embodiment support shoulders (50) are located on the outside of the valve (24) where the conical receiving area (34) tapers into the sealing neck (36) as shown in FIGS. 1 and 2. The support shoulders (50) do not extend outward beyond the widest portion of the sealing chamber (48) or downward around the outside surface of the sealing chamber (48) to increase the overall diameter of the valve (24).

Figure 7:
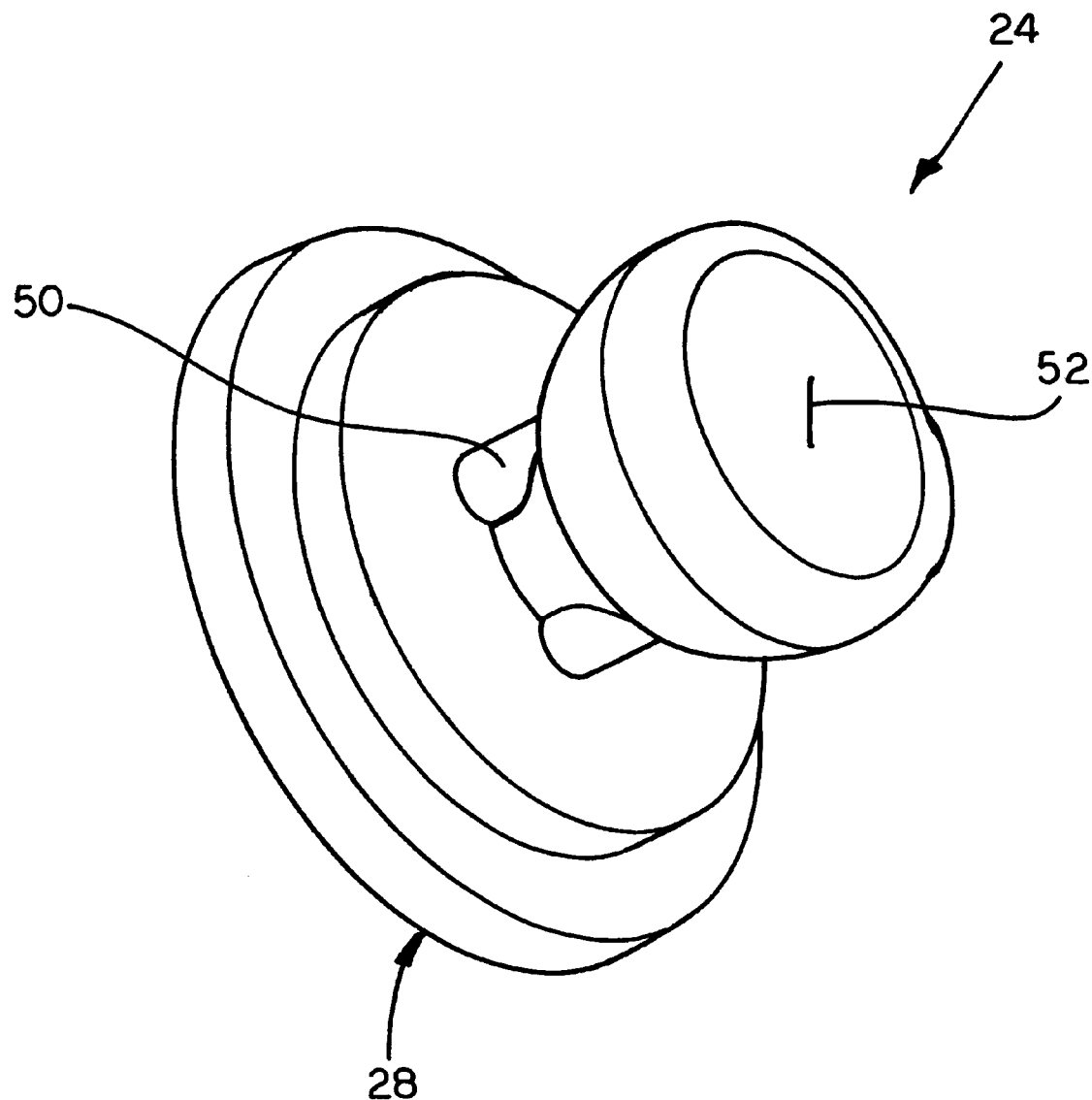
FIG. 7 is a perspective view of the valve of the present invention showing the support shoulders.

Specifically, the support shoulders (50) do not increase the outside diameter of that portion of the seal containing the sealing chamber (48). Also, the support shoulders (50) do not extend downward beyond the widest portion of the outside of the sealing chambers (48), thus avoiding undue expansion of the neck opening (38) against the side walls of the valve housing (14) upon insertion of a cannula. As a result, when a catheter is inserted through the neck opening (38), the neck area will not unduly bulge out and come into contact with the walls of the valve housing (14). The support shoulders (50) also prevent the valve (24) from extending excessively downward toward the second opposing open end (18) of the valve housing and, importantly, provide support for the seal on insertion and removal of catheters through the valve (24). Two or more support shoulders are supplied on the outside of the seal, but preferably four support shoulders are used to provide maximum support for the seal. When four support shoulders are used, preferably two are located perpendicular to the slit (52) and two in line with the slit (52) as shown in FIG. 7.

The single slit (52) and the lips (54) and (56) are forced open by a dilator, guidewire or catheter inserted into the body of the hemostasis cannula unit and through the valve (24). The spacial geometry of the walls of the semi-spherical sealing chamber (48) strongly force opposing sealing lips (54) and (56) into a normally closed position and hold them in that position to prevent an external reverse flow of blood. Likewise, when the sealing lips (54) and (56) are opened after a catheter is inserted, the opposing forces of the sealing neck (36) seal around the catheter and halt the reverse flow of blood.

The sealing lips which are shown in the form of a pair of opposing lips (54) and (56) may also take the form of three to six separate lips formed from either "y", "cross" shaped or star/spoke slits. However, two lips (which are formed by a single slit) are preferred because they provide the maximum amount of sealing pressure from the semi-spherical walls of the sealing chamber (48) when a catheter is not in place in the hemostasis cannula unit. It is also preferred that the slit length be within about 0.020 to 0.080 inch (0.051 cm. to 0.203 cm.).

The outside diameter of the sealing chamber (48) should be less than the diameter of the longitudinally extended hemostasis valve housing (14) so as to insure that, even upon insertion of a catheter into the valve (24), the body of the valve (24) will not expand against the interior walls of the valve housing (14) thereby increasing the difficulty of catheter insertion and the likelihood of hemodynamic pressure dampening. Because of their location adjacent to the sealing neck (36), the support shoulders (50) also do not extend the diameter of the sealing chamber (48) of the valve (24) to the interior walls of the valve housing (14).

The valve housing (14) is longitudinally extended to form a valve chamber (58) having first (16) and second (18) openings which allow a catheter to be inserted through the chamber. Preferably, access to the interior of the chamber is also provided through a port (60) to which is attached a fitting (62) that facilitates attachment of tubing to permit insertion or withdrawal of fluids from the chamber (58) during use.

The valve housing (14) of the hemostasis cannula unit (10) is also preferably provided with a suture ring (64) to allow temporary attachment of the cannula unit directly to a patient's body to provide stabilization of the hemostasis cannula unit.

The final element of the hemostasis cannula unit of the present invention is the sheath (26) onto which the valve housing (14) may be attached. The sheath preferably is provided with a tapered distal tip (66), in the preferred use to closely fit onto a dilator which is inserted through the cannula for initial introduction into a body vessel.

In the preferred means of operation, a needle is inserted into a patient's blood vessel. Through the lumen of the needle a guidewire is in turn inserted into the blood vessel. The needle is removed. The hemostasis cannula unit (10) of the present invention is then prepared by inserting a dilator through the cap opening (16), the valve (24), out the second opening (18) through the sheath (26) and out the distal end of the sheath. The sheath (26) and dilator are designed such that the tapered distal tip (66) snugly fits around the dilator.

The dilator and hemostasis cannula unit (10) are advanced as a unit onto the guidewire and into the blood vessel. The dilator tip, which is tapered, increases the size of the opening in the blood vessel as it enters the vessel so that ultimately an opening large enough to accommodate the sheath (26) is formed. After the sheath is inserted into the blood vessel, the dilator and guidewire are removed, leaving in place the hemostasis cannula unit (10) of the present invention.

With the hemostasis cannula unit thus in place, it is possible to insert guidewires and catheters having a wide range of diameters with ease. A catheter is inserted through the first opening (16) in the cap (12) and into the valve (24). If the catheter is inserted slightly off center, it will be guided to the neck opening (38) by means of the conical receiving area (34). The catheter is then moved through the passageway (40) of the sealing neck (36) into the semi-spherical sealing chamber (48) and out through the sealing lips (54) and (56). After exiting through the sealing lip (54) and (56), the catheter is advanced out the opening (18) down through the sheath (26) and into the blood vessel. Any blood which flows between the sheath and the catheter and up into the interior of the valve chamber (58) is not permitted to escape to the exterior because of the sealing action of the narrowed portion (42) or portions of the sealing neck (36) around the body of the catheter as shown in FIGS. 2, 3, and 4. By providing narrowed (42) and broadened (44) portions of the sealing neck (36), there is a reduced surface area of the inside surface of the sealing neck (36) against any guidewire or catheter which passes through the seal. It has been surprisingly discovered that by reducing the amount of this contact surface area, there is reduced resistance to the movement of the guidewire or catheter through the sealing neck (36) while at the same time a good seal is maintained to prevent the flow of blood through the valve (24).

Support for the valve (24) as the catheter is being inserted is provided by the support shoulders (50). The support shoulders (50) do not extend downward onto the outside surface of the sealing chamber (48) so that a consistent overall outside diameter of the valve (24) is maintained from the neck opening (38) through the sealing chamber (48). The support shoulders (50) reduce the insertion and withdrawal forces making insertion and withdrawal easier, providing better "feel" for the medical personnel. The support shoulders (50) also provide excellent support for the valve (24) to prevent collapse while in use.

Figure 5:
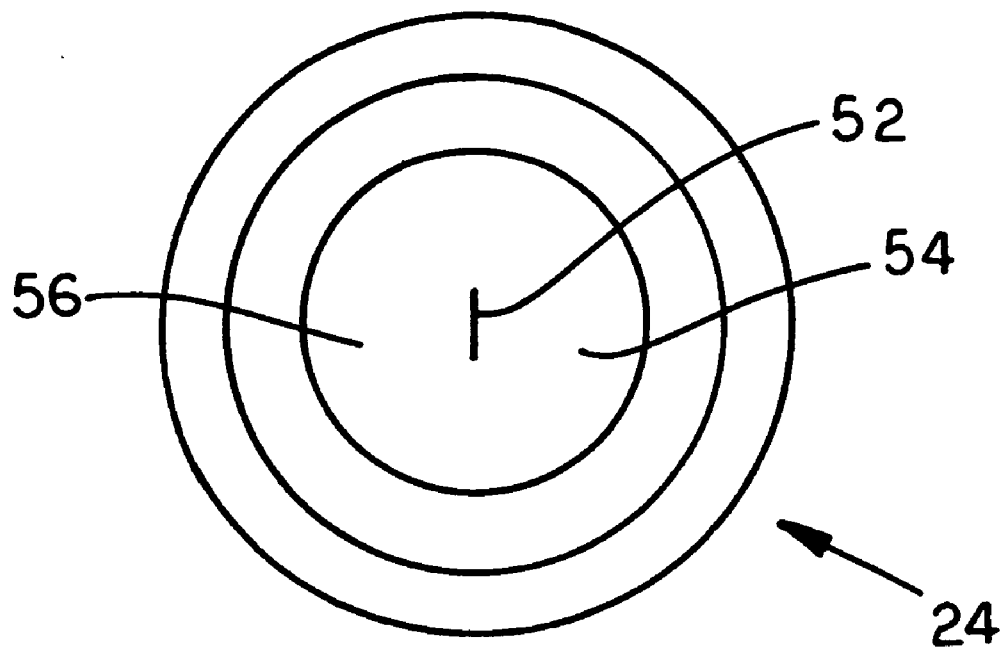
FIG. 5 is a bottom view of the one-piece valve of the present invention.

In FIG. 5, which is a bottom view of the valve (24) of the present invention, the sealing lips (54) and (56) are shown along with the slit (52).

Figure 6:
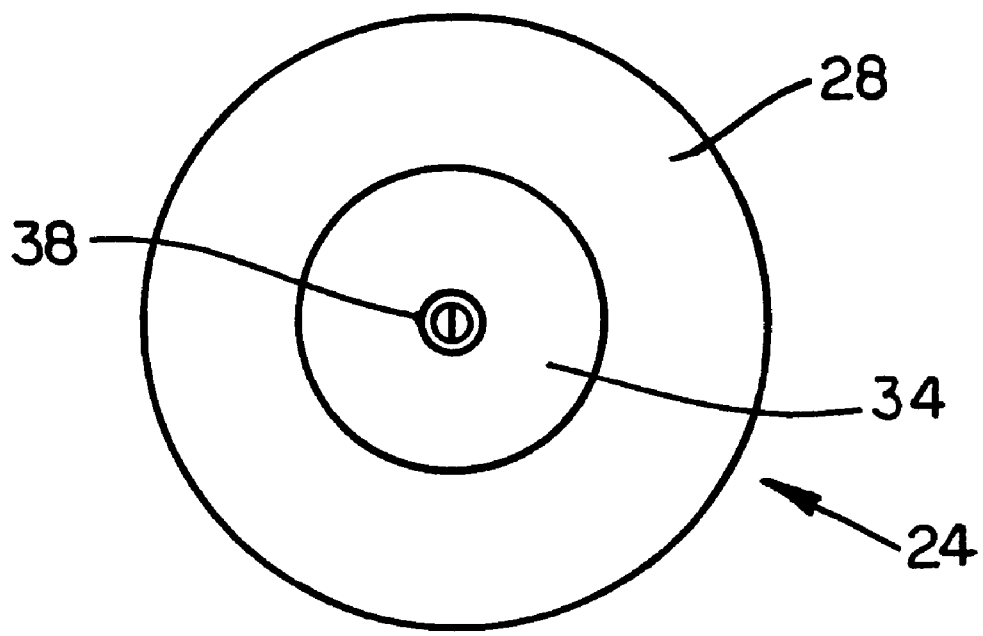
FIG. 6 is a top view of the valve of the present invention.

In FIG. 6, which is a top view of the valve (24) of the present invention, the conical receiving area (34) of the valve (24) is illustrated along with the neck opening (38).

In FIG. 7, which is a side perspective view of the valve (24) of the present invention, the support shoulders (50) and their location on the valve (24) is disclosed.

Thus, the present invention provides a sealing mechanism for a hemostasis valve unit such that:

1. is universal, i.e., useful with both guidewires and with catheters having a wide range of diameters;
2. provides relatively easy insertion and withdrawal of varying diameters of catheters and guidewires;
3. is free from excessive restriction which would cause hemodynamic dampening;
4. has sufficient strength not to collapse on the insertion and removal of the various medical devices during the introduction of catheters into blood vessels;
5. will seal or achieve hemostasis if no device is present in the valve and after removal of devices from the cannula unit;
6. is self-centering when guidewire is inserted;
7. provides hemostasis during manipulation of guidewire; and
8. provides for multiple exchanges of devices without significant degradation of performance.

By employing this hemostasis valve, it is possible to use different catheters and guidewires which may vary in diameter. The valve of the present invention is particularly useful because it provides for good sealing, even around relatively small diameter guidewires. In addition, the universal hemostasis valve of the present invention has excellent "feel" and a reduced incidence of hemodynamic pressure dampening for a wide range of catheter diameters. This improved hemostasis valve does not collapse under use even when catheters and guidewires with varying diameters are employed and surprisingly retains an improved ease of insertion and withdrawal over prior art hemostasis valves because of the reduced contact between the surface of the sealing neck and the guidewire being inserted therethrough.

The present embodiment of the present invention is considered to be merely illustrative and changes may be made in its specific form without departing from the spirit or essential characteristics of this invention.

What is claimed:

1. A hemostasis valve for receiving an inserted guidewire and catheter comprising:
   (a) a sealing neck comprising a narrowed portion and a broadened portion,
   (b) a sealing chamber broader than the sealing neck, wherein the sealing chamber communicates with the sealing neck, and
   (c) sealing exit lips communicating with the sealing chamber,
   wherein the narrowed portion of the sealing neck is secured to the sealing chamber and the broadened portion of the sealing neck communicates with a conical receiving area.

2. The hemostasis valve of claim 1 wherein the conical receiving area is secured to the sealing neck.

3. The hemostasis valve of claim 1 further comprising support shoulders secured to an outside surface of the hemostasis valve adjacent to the sealing neck.

4. The hemostasis valve of claim 1 wherein the sealing neck further comprises a passageway, wherein the passageway communicates between a conical receiving area and the sealing chamber, wherein the narrowed portion of the sealing neck communicates with the sealing chamber and the broadened portion of the sealing neck communicates with the conical receiving area.

5. The hemostasis valve of claim 1 wherein the sealing neck further comprises a passageway, wherein the passageway communicates between a conical receiving area and the sealing chamber, wherein the narrowed portion of the sealing neck communicates with the conical receiving area and a broadened portion of the sealing neck communicates with the sealing chamber.

6. The hemostasis valve of claim 1 wherein the passageway of the narrowed portion has a diameter smaller than the diameter of a guidewire.

7. The hemostasis valve of claim 1 wherein the sealing lips are formed from a slit in a flattened section of the sealing chamber.

8. The hemostasis valve of claim 1 further comprising a second narrowed portion adjacent to the sealing neck.

9. A hemostasis valve for receiving an inserted guidewire and catheter comprising
   (a) a sealing neck comprising a narrowed portion and a broadened portion,
   (b) a sealing chamber broader than the sealing neck, wherein the sealing chamber communicates with the sealing neck, wherein the narrowed portion of the sealing neck is secured to the sealing chamber and the broadened portion of the sealing neck communicates with a conical receiving area,
   (c) sealing exit lips communicating with the sealing chamber, and
   (d) support shoulders secured to an outside surface of said hemostasis valve adjacent to the sealing neck.

10. The hemostasis valve of claim 9 wherein a conical receiving ar ea is secured to the sealing neck.

11. The hemostasis valve of claim 9 wherein the sealing neck comprises an elongated sealing neck with a passageway which communicates between a conical receiving area and the sealing chamber, a narrowed portion communicating with the sealing chamber and the broadened portion communicating with the conical receiving area.

12. The hemostasis valve of claim 9 wherein the sealing neck comprises an elongated sealing neck with a passageway which communicates between a conical receiving area and the sealing chamber, a narrowed portion communicating with the conical receiving area and the broadened portion communicating with the sealing chamber.

13. The hemostasis valve of claim 9 wherein the passageway of the narrowed portion has a diameter smaller than a diameter of a guidewire.

14. The hemostasis valve of claim 9 wherein the sealing lips are formed from a slit in a flattened section of the sealing chamber.

15. A hemostasis cannula unit comprising
   (a) a longitudinally extended valve housing having a first opening and a second opening,
   (b) a cap enclosing the first opening of the valve housing and providing a hole to permit the insertion of a medical device into the housing's first opening through the central chamber and out the opposite second opening, and
   (c) a hemostasis valve located within said central chamber, wherein said hemostasis valve comprises a sealing neck for sealing around an inserted device, a sealing chamber communicating with the sealing neck and sealing exit lips communicating with the sealing chamber, wherein the sealing neck comprises an elongated sealing neck with a passageway therethrough, containing narrowed and broadened portions of the passageway wherein the narrowed portion of the sealing neck is adjacent to the sealing chamber and the broadened portion of a sealing neck communicates with the conical receiving area.

16. The hemostasis valve of claim 15 wherein a conical receiving area is secured to the sealing neck.

17. A hemostasis valve for receiving an inserted guidewire and catheter comprising:
   (a) a sealing neck, wherein the sealing neck comprises a pair of narrowed portions,
   (b) a sealing chamber communicating with the sealing neck, and
   (c) sealing exit lips communicating with the sealing chamber.

18. The hemostasis valve of claim 17 wherein a broadened portion is located between the narrowed portions.

19. The hemostasis valve of claim 17 wherein the sealing neck further comprises three narrowed portions and two broadened portions.

20. A hemostasis valve for receiving an inserted guidewire and catheter, comprising:
   (a) a sealing neck, wherein the sealing neck comprises a pair of narrowed portions,
   (b) a sealing chamber communicating with the sealing neck,
   (c) sealing exit lips communicating with the sealing chamber, and
   (d) support shoulders secured to an outside surface of said hemostasis valve adjacent to the sealing neck.

21. The hemostasis valve of claim 20 further comprising a broadened portion located between the narrowed portions.

22. The hemostasis valve of claim 20 wherein the sealing neck further comprises three narrowed portions and two broadened portions.

23. A hemostasis valve for receiving an inserted guidewire and catheter, comprising:
   (a) a sealing neck comprising a narrow portion and a broadened portion with an end,
   (b) a sealing chamber communicating with the sealing neck,
   (c) sealing exit lips communicating with the sealing chamber, and
   (d) a separate and distinct conical receiving area communicating with the end of the sealing neck.

24. A hemostasis valve for receiving an inserted guidewire and catheter, comprising:
   (a) a sealing neck having an end, wherein the sealing neck comprises a pair of narrowed portions and a broadened portion located between the narrowed portions,
   (b) a sealing chamber communicating with the sealing neck,
   (c) sealing exit lips communicating with the sealing chamber,
   (d) support shoulders secured to an outside surface of said hemostasis valve adjacent to the sealing neck, and
   (e) a separate and distinct conical receiving area communicating with the end of the sealing neck.

25. A hemostasis valve for receiving an inserted guidewire and catheter comprising
   (a) a conical receiving area,
   (b) a sealing neck, wherein the sealing neck comprises a narrowed portion and a broadened portion, wherein the sealing neck communicates with the conical receiving area,
   (c) a sealing chamber communicating with the sealing neck, and
   (d) sealing exit lips communicating with the sealing chamber
   wherein the sealing neck further comprises a passageway, wherein the passageway communicates between the conical receiving area and the sealing chamber and wherein the narrowed portion of the sealing neck is secured to the sealing chamber.

* * * * *